Aug. 9, 1955 G. MERRILL Plant Pat. 1,410

NECTARINE TREE

Filed Oct. 28, 1954

WITNESS

Addison E. Avery

INVENTOR

Grant Merrill

Webster & Webster

ATTYS.

United States Patent Office

Plant Pat. 1,410
Patented Aug. 9, 1955

1,410

NECTARINE TREE

Grant Merrill, Red Bluff, Calif.

Application October 28, 1954, Serial No. 465,457

1 Claim. (Cl. 47—62)

This invention relates to a new and distinct variety of nectarine tree which bears large, firm, yellow fleshed, highly colored, fine flavored fruit which is a clingstone when hard ripe and a freestone when soft ripe.

One of the distinguishing characteristics of the present variety of nectarine tree is that it has a relatively early ripening period, being in harvest substantially with the John Rivers nectarine (unpatented), and about a week or ten days later than the Merrill Sunrise nectarine (United States Plant Patent No. 1256).

Another distinguishing characteristic of the present nectarine tree is that the fruit is extremely firm when very highly colored; thus being especially desirable not only for local market, but for long distance shipping.

A further distinguishing characteristic of the present necatrine tree is that fruit ripened in the full sun is nearly completely over-spread with mahogany-red, while on fruit in shady portions of the tree the red may be one-half to three-fourths over-spread.

As compared to the John Rivers nectarine, the present variety of nectarine tree bears yellow instead of white fleshed fruit, and which is of much more desirable quality for the market, particularly with respect to size, skin and flesh color, and firmness.

As compared to the Merrill Sunrise nectarine, there is a general resemblance of the fruit, except that here—in addition to ripening a week or ten days later, as aforesaid—the fruit is somewhat larger, and is usually a little longer than wide, whereas the converse is normally true of the Merrill Sunrise nectarine. In addition, the fruit of the instant variety of nectarine has a somewhat similar color to the Merrill Sunrise nectarine, but has less yellow flecking on the skin and more of a mahogany red than a brownish red color; the flavor and aroma being higher and unusually good for a yellow fleshed nectarine.

The herein claimed variety of nectarine tree was originated by me, under careful controls and continuing inspection in my experimental orchard near Red Bluff, California, as a second generation, open-pollinated blossom, seedling of a cross of the J. H. Hale peach (unpatented) and the Flaming Gold nectarine (unpatented).

Such cross produced a quantity of seeds, which were planted and resulted in first generation seedlings. Seeds from the same, with open-pollinated blossoms, produced second generation seedlings. One of the latter was observed to be a vigorous grower and evidenced desirable fruit characteristics, particularly as to the period of ripening and the quality of the fruit. This particular second generation seedling was therefore selected by me for propagation, and which is the present variety.

Asexual reproduction was accomplished by grafting onto mature Golden Jubilee (unpatented) peach trees in such experimental orchard. These grafts, in comparison with the parent tree, were found to carry forward each and every one of the characteristics of the same.

Figures 1, 2:
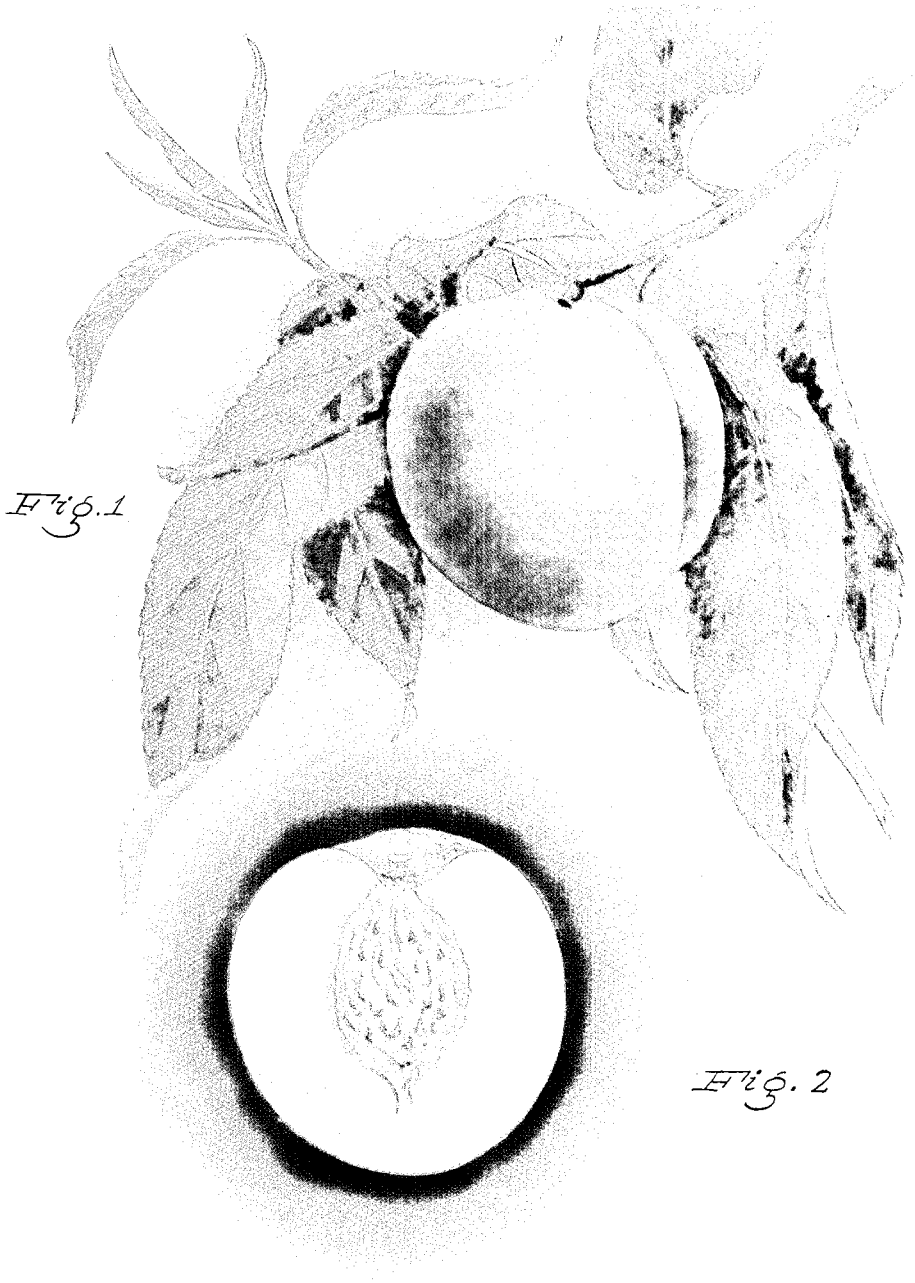
Fig. 1 is an elevation of one of the fruit, together with a twig on leaves.
Fig. 2 is a sectional elevation of one of the fruit, with the stone exposed.

Referring now more specifically to the pomological details of this new and distinct variety of nectarine tree, the following is an outline description thereof; all major color plate identifications being by reference to Maerz and Paul Dictionary of Color:

Tree: Large size; vigorous growth; spread normal; form and density controlled by pruning; very productive; regular bearer.

*Trunk.*—Medium stocky; texture—shaggy.

*Branches.*—Medium stocky; color—reddish brown.

*Lenticels.*—Medium number; medium size.

*Leaves.*—

Size—Medium; average length—5½″ to 6″; average width—1½″ to 1¾.″

Form—Lanceolate; tip accuminate; medium thickness.

Texture—Rugose along midriff only.

Margin—Crenate.

Petiole—Medium length; medium width.

Glands—None to five—average three; alternate; medium to large size; reniform; green; positioned at base of leaves and upper part of petiole.

Stipules—On new leaves dropping early.

Color—Top side—medium green (22–L–7); under side—lighter green (21–J–6).

Flower buds: Medium size; medium length; plump; free.

Flowers: Dates of first and last bloom—March 1, 1954, and March 15, 1954, respectively.

*Size.*—Large.

Color—Light pink to salmon; pollen fertile; unopened anthers—orange yellow.

Pollen—present.

Fruit:

*Maturity when described.*—June 28, 1954—eating to soft ripe.

*Date of first picking.*—June 20, 1954.

*Date of last picking.*—June 27, 1954.

*Size.*—Large; fairly uniform; average cheek to cheek diameter—2⅛″ to 2½″; average transversely in suture plane—2¼″ to 2⅝″; average length—2¼″ to 2¾″.

*Form.*—Somewhat variable; typically ovoid to ovate, but sometimes globose.

*Suture.*—A distinct but shallow line extending from base to apex, with little or no depression beyond pistil point. Often very deep, almost to pit, at stem end.

*Ventral surface.*—Usually rounded; strong lipped throughout; lips slightly unequal.

*Cavity.*—Normally rounded, usually a deep crease on the suture side; average depth—⅜″ to ½″; average spread—⅜″ to ¾″; markings—green to full red blush.

*Base.*—Truncate to slightly retuse.

*Apex.*—Retuse.

*Pistil point.*—Apical.

*Skin.*—Medium thickness; tender; free when soft ripe.

Tendency to crack—Light to considerable at the apex on very large fruit only.

Color—(10–L–2) over-spread to a major extent with red (4–L–10), shading to a deep mahogany (7–L–6), sometimes with yellow flecking, especially on the largest fruit, and more so on fruit from rank growing young grafts.

*Flesh.*—

Surface to pit cavity—Yellow, with very slight green cast on soft ripe fruit.

Amygdalin—Moderate.
Juice—Abundant.
Texture—Fine, meaty to melting when full ripe.
Fibers—Tender; few.
Ripens—Evenly.
Flavor—Delicate; vinous.
Aroma—Pronounced.
Eating quality—Best.
Color—Yellow (9–K–3), shading outwardly from stone to somewhat darker yellow (9–L–5 to 9–L–7), slight green cast near the pit cavity before softening of the flesh, but when softened the green almost disappears. Sometimes slight red (4–L–6) in the flesh near the tip of the stone.

*Stone.*—Cling to hard ripe, free when soft ripe. Retains short fiber-like threads at the stem end.
Size—Medium; average length—1¼″ to 1½″; average breadth—1″ to 1⅛″; average thickness—⅝″ to ¾″.
Form—Obovoid; cuneate towards base.
Base—Straight, sometimes slightly oblique.
Hilum—Oval.
Apex—Acuminate.
Sides—Equal to unequal.
Surface—Regularly furrowed towards apex; ridged towards apex; pitted toward base.
Pits—Circular to elongated.
Ventural edge—Thick, usually without wing towards base.

Dorsal edge—Full, with deep broad grooves toward base.
Ridges—Rounded; on either side; continuous.
Tendency to split—Slight.
Color—Light tan (10–E–4 shading to 11–C–9).

Use: Market—local and long distance shipping; dessert; culinary.
Keeping quality: Good.
Shipping quality: Excellent.

The tree and its fruit herein described may vary in slight detail due to climatic and soil conditions under which the variety may be grown.

Having thus described my invention, I claim:

A new and distinct variety of nectarine tree as illustrated and described, which bears large, yellow fleshed, highly colored, fine flavored fruit which is a clingstone when hard ripe and a freestone when soft ripe; characterized in comparison to the Merrill Sunrise nectarine by larger fruit, higher flavor and aroma, being longer than wide on the average, whereas the Merrill Sunrise is normally of converse dimensioning, having yellow skin—with less yellow flecking—over-spread to a major extent with a mahogany-red rather than a brownish-red, and ripening a week or ten days later and approximately with the John Rivers nectarine; and further characterized by fruit which is extremely firm when very highly colored.

No references cited.